US008156829B2

(12) United States Patent
Smyth et al.

(10) Patent No.: US 8,156,829 B2

(45) Date of Patent: Apr. 17, 2012

(54) METHODS OF ACOUSTIC MEASUREMENT AND CONTROL OF PHARMACEUTICAL SPRAYS

(75) Inventors: Hugh D. C. Smyth, Albuquerque, NM (US); Anthony J. Hickey, Chapel Hill, NC (US); Sorin M. Mitran, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1123 days.

(21) Appl. No.: 11/666,366

(22) PCT Filed: Oct. 26, 2005

(86) PCT No.: PCT/US2005/038698

§ 371 (c)(1),
(2), (4) Date: Oct. 26, 2007

(87) PCT Pub. No.: WO2006/047660

PCT Pub. Date: May 4, 2006

(65) Prior Publication Data

US 2008/0121228 A1 May 29, 2008

Related U.S. Application Data

(60) Provisional application No. 60/622,244, filed on Oct. 26, 2004.

(51) Int. Cl.
*G01N 15/02* (2006.01)
*A61M 11/00* (2006.01)

(52) U.S. Cl. .................................. 73/865.5; 128/200.16

(58) Field of Classification Search .............. 128/200.16
See application file for complete search history.

(56) References Cited

U.S. PATENT DOCUMENTS 6,196,218 B1 * 3/2001 Voges ...................... 128/200.14
7,066,029 B2 * 6/2006 Beavis et al. ................... 73/649
7,347,201 B2 * 3/2008 Djupesland .............. 128/200.23
7,543,581 B2 * 6/2009 Djupesland .............. 128/200.14
2004/0091541 A1 5/2004 Unger

OTHER PUBLICATIONS

International Search Report and Written Opinion dated May 16, 2006.

International Preliminary Report on Patentability dated May 1, 2007.

Crowder TM, Louey MD, Sethuraman VV, Smyth HDC, Hickey AJ (2001) "2001: An Odyssey in Inhaler Formulations and Design," *Pharmaceutical Technology*, 25(7), 99-113.

Garcia-Contreras, Lucila and Smyth, HDC (2005) *Am. J. Drug Delivery*, "Liquid-Spray or Dry-Powder Systems for Inhaled Delivery of Peptide and Proteins?" 3(1), 29-45.

Smyth, HDC, Beck VP, Williams D, Hickey AJ (2004) "The Influence of Formulation and Spacer Device on the in Vitro Performance of Solution Chlorofluorocarbon-Free Propellant-Driven Metered Dose Inhalers," *AAPS PharmSciTech*, 5(1) Article 7.

Smyth, HDC: (2003) "The Influence of Formulation Variables on the Performance of Alternative Propellant-Driven Metered Dose Inhalers," *Advanced Drug Delivery Reviews*, 55(7), 807-828.

Smyth HDC, Hickey AJ (2003) "Multimodal Particle Size Distributions Emitted From HFA-134a Solution Pressurized Metered-Dose Inhalers," *AAPS PharmSciTech*, 4(3), Article 38.

Smyth HDC et al. (2006) "Influence of Actuator Design on Spray Pattern Analysis of Metered Dose Inhalers," *Respiratory Drug Delivery X*, pp. 1-4.

Smyth HDC et al. (2006) "Spray Pattern Analysis for Metered Dose Inhalers: Effect of Actuator Design," *Pharmaceutical Research*, (PROOF) pp. 1-7.

* cited by examiner

*Primary Examiner* — Daniel Larkin

(74) *Attorney, Agent, or Firm* — Jenkins, Wilson, Taylor & Hunt, P.A.

(57) ABSTRACT

Methods of modulating a characteristic of a pharmaceutical compound spray by acoustic measurement and control of the pharmaceutical spray are disclosed. The methods include analyzing a selected characteristic of a pharmaceutical compound spray utilizing acoustic measurement to develop corresponding acoustic data. The methods further include controlling the selected characteristic by applying acoustic excitation to the pharmaceutical compound spray in accordance with the acoustic data developed.

23 Claims, 12 Drawing Sheets

METHODS OF ACOUSTIC MEASUREMENT AND CONTROL OF PHARMACEUTICAL SPRAYS

CROSS-REFERENCE TO RELATED APPLICATION

This application claims the benefit of U.S. Provisional Patent Application Ser. No. 60/622,244, filed Oct. 26, 2004; the disclosure of which is incorporated herein by reference in its entirety.

TECHNICAL FIELD

The subject matter disclosed herein relates generally to pharmaceutical compound delivery and performance, and more particularly to methods of acoustic measurement and control of pharmaceutical sprays.

BACKGROUND

Control of the drug delivery and performance aspects of pharmaceutical products is critical for safety and efficacy and as such, pharmaceutical products are among the most highly regulated products in the world. This need to control drug delivery characteristics has increased in recent years with the development of increasingly potent active pharmacological agents (e.g., proteins, peptides, nucleic acid biotech therapies, etc.) and the narrowing of the therapeutic window of these agents.

In the fields of drug delivery and pulmonary therapy, inhaled pharmaceutical aerosols are a common and rapidly growing platform for the delivery of drugs and other medicaments and can provide significant therapeutic benefits. To realize those benefits, there have arisen a variety of inhaler devices for administration and delivery of drug therapies via aerosol-based inhalation.

The most common type of inhaler device used is the pressurized metered dose inhaler (pMDI), which is typically associated with asthma treatments. This type of inhaler typically uses an ozone-depleting CFC propellant such as Freon, but recent pMDI systems have used alternatives such as hydrofluoroalkane (HFA) propellant in lieu of CFC propellant. A second type of inhaler device is the nebulizer. In operation, nebulizers deliver droplets in a size range that enables the drug to reach the periphery of the lung through the air passage of a patient. A third type of inhaler device is a dry powder inhaler (DPI). Typically, DPIs are configured to deliver a powdered drug or drug mixture which includes an excipient and/or other ingredients. It is additionally understood that typical inhaler devices, including those discussed above, may include continuous valve emission inhalers or dose metering valve emission inhalers.

As discussed above, pressurized metered dose inhalers (pMDIs) are important in disease therapy (e.g., for asthma or other chronic obstructive pulmonary disease) as they are the most widely used respiratory drug delivery device, with an estimated 800 million units produced yearly. However, less than a quarter of the emitted dose of the aerosol produced by a pMDI device typically reaches the lungs. As shown in FIG. 1, previous experimental work has shown the presence of a bimodal particle size distribution in the sprays produced by pMDI devices using hydrofluoroalkane (HFA) 134a propellant (from 50% w/w to 97.5% w/w). One peak of the droplet diameter (D) distribution is typically located at D~1 μm and another peak at D~10 μm. The large separation of droplet sizes is particularly significant for inhaled therapy since particles in the large diameter range (>5 μm) are non-respirable. Based on this consideration, design goals for inhalation aerosols is to maximize the respirable lung deposition of particles (generally particles in the range of 1-5 μm) and minimize throat deposition (typically particles >5 μm) using materials and substances that have established safety profiles for administration to the airways. As such, there is considerable interest in devising mechanisms that would cause further break-up of the large diameter particles observed in inhalation aerosol sprays.

Pressurized metered dose inhaler (pMDI) devices typically incorporate a propellant, under pressure, to generate a metered dose of an aerosol through an atomization nozzle. Referring to FIG. 2, a typical prior art pMDI, generally shown as 10, can consist of several components. Upon actuation of an actuator 12 by a patient, a metered volume (typically between 20-100 μl) of a drug/excipient/propellant blend 13 is expelled from a canister 14 via a valve, such as metering valve 16. The metered volume passes through an atomization orifice 18 where primary atomization occurs and whereby the metered volume is transformed into an aerosol spray plume consisting of individual atomized droplets. A typical pMDI 10 can further comprise a spacer 22 chamber for increasing the distance between atomization orifice 18 and the throat of a patient, thereby improving peripheral lung deposition.

The interaction of a dynamic aerosol plume with the geometry of the mouth and airways determines the extent of oral and lung deposition. Mechanisms of particle deposition include inertial impaction, sedimentation, diffusion, interception, and electrostatic precipitation. The relative importance of each deposition mechanism on an individual droplet depends on a multitude of factors such as droplet size, velocity, evaporation rates, and the anatomical features of the patient's airways.

Typically, particle size is one of the most important parameters in determining the effectiveness of inhaled pharmaceutical aerosols since particle size may determine where aerosols will deposit in the lungs. Referring to FIG. 3, the regional lung deposition fraction of aerosols in different regions of the airway is outlined as a function of median aerodynamic particle diameter. Optimized deposition pattern (mass deposited in pulmonary region versus mass deposited elsewhere) occurs when particle diameters are between 0.5 and 5 microns (μm). It is additionally understood that for drug delivery, it is the mass of drug that is important for pharmacological effect (i.e., though pulmonary deposition efficiency increases at smaller particle sizes, these size ranges do not contain adequate drug doses for clinically relevant delivery). Knowledge of this particle size dependency on regional lung deposition has lead to a general goal for pMDI design in order to generate aerosol droplets between 1-5 microns (μm) aerodynamic diameter. It has been determined that pharmaceutical spray droplets of this size are of sufficient mass and have a greater probability to deposit in the lungs rather than mouth and throat regions, resulting in higher drug efficiency.

The performance of prior art pMDIs with respect to formulation and device design has been reviewed, indicating only 5-25% of the dose is deposited in the lungs. Similarly, with other types of inhalers (i.e., dry powder inhalers), less than 30% of the dose reaches the lungs. Most of the drug is deposited in the mouth and throat due to inertial impaction of large (>5 μm) particles. For example, the inefficiencies of typical prior art inhalers used for respiratory drug delivery are shown in FIG. 4, which illustrates a comparison of the quantity and percent of a nominal dose of albuterol deposited in the lungs, oropharynx, apparatus, and exhaled, with typical use of a dry powder inhaler (DPI), a pressurized metered-dose inhaler (pMDI), a pMDI with holding chamber (MDI/HC), and a nebulizer (NEB). As shown in FIG. 4, both the DPI and pMDI deposit greater than 50% of nominal dose in the oropharynx, while the MDI/HC and NEB leave 66-78% of the dose in the apparatus.

The fundamental mechanisms associated with the atomization of metered volumes of superheated liquid propellants have also previously been studied. The discharge from an actuator orifice has been shown to be choked and mass limited. As propellant begins to exit the atomization orifice, incipient cavitation occurs and liquid propellant is dispersed with rapidly growing bubbles. It has been shown that this bubble growth occurs in turbulent flow regimes. Despite this complexity, past research has attempted to model and predict aerosol respirability although post-nozzle droplet break-up has not been well studied in pMDIs. Theoretical calculations made previously indicate that large droplets emitted from pMDIs will impact on the mouth/throat before undergoing particle size reduction via aerodynamic loading/post nozzle breakup. Additional research of particle size distributions emitted from pMDIs indicate that there is a significant proportion of the aerosol in this large droplet size range of such a size that will not be respirable. Collectively, these observations present significant challenges for improving the efficiency of pMDI output.

Measurement and diagnostic techniques characterizing pharmaceutical sprays are additionally of importance due to the need to ensure sprays meet quality, regulatory, and performance criteria. The most important parameters used to quantify inhaler performance are particle size and size distribution, emitted dose, and fine particle dose (mass of drug with particle size less than 5 μm). Various methods have been employed in the past to analyze such aerosol particle characteristics. Inertial impaction particle size analysis is performed regularly on pharmaceutical inhalation aerosols because it yields aerodynamic particle sizes that are pertinent to the function of this type of aerosol. These methods are time consuming, influenced by ambient humidity, and subject to subtleties in methodology (particle overload, sampling operator effects, etc.). Direct visualization of particles is also performed using microscopy techniques and image analysis software. In addition to being highly time consuming, there are limitations to the number of particles that can be analyzed for statistical validity. Light scattering methods such as laser diffraction are also commonly used techniques. One such technique is phase-Doppler particle analysis (PDPA), a single particle light scattering technique that provides the simultaneous measurement of drop size, velocity, and concentration to yield detailed temporal and spatial analysis of pharmaceutical sprays. Most laser techniques are not capable of analysis of the entire aerosol and these measurements are also significantly influenced by the manufacturer, model, and algorithm used to convert light scattering measurements to particle size distributions. All of the measurement techniques commonly employed have limitations due to specific principles of measurement, or other variations, and they are further not suitable for diagnosis of inhaler spray droplet sizes in-situ. Therefore, there remains a need for novel methods to measure aerosolization efficiency and spray characteristics, such as particle size distributions.

Furthermore, the control of pharmaceutical sprays during atomization has not been described in the prior art. Post-atomization methods include various spacer devices, such as spacer chamber 22 shown in FIG. 2, designed to increase time for droplet evaporation and deceleration of aerosol plumes emitted from pMDIs. However, as illustrated in FIG. 4, holding chamber/spacer devices (MDI/HC) result in minimal increases in lung delivery. Changes in orifice size and formulation composition are also limited in their influence of modulation of pMDI aerosols. As such, there additionally remains a long-felt need for novel methods to further break-up aerosols emitted from inhaler devices, such as pMDIs, such that they can be delivered to the intended site of action (e.g., the lung) in high efficiency form.

SUMMARY

In one embodiment of the present subject matter, a method is provided for modulating a characteristic of a pharmaceutical compound spray to be delivered to a patient from an inhaler device. The method includes analyzing a selected characteristic of a pharmaceutical compound spray utilizing acoustic measurement to develop corresponding acoustic data, and the method then further includes controlling the selected characteristic by applying acoustic excitation to the pharmaceutical compound spray in accordance with the acoustic data developed.

In a further embodiment of the present subject matter, a method is provided for modulating spray particle size characteristics of a pharmaceutical compound spray to be delivered to a patient from an inhaler device. The method includes analyzing spray particle size characteristics of a pharmaceutical compound spray by measuring an overall acoustic emission pattern emitted by the spray to develop corresponding acoustic data. The method additionally includes controlling the spray particle size characteristics by applying acoustic excitation to the pharmaceutical compound spray in accordance with the acoustic data developed. The method further includes synthesizing the analyzing and controlling steps, thereby forming an active feedback system.

In another embodiment of the present subject matter, a method is provided for modulating spray particle size characteristics of a pharmaceutical compound spray. The method includes providing an inhaler device adapted to deliver a pharmaceutical compound spray to a patient. The method additionally includes determining a desired spray particle size of individual droplets of the pharmaceutical compound spray. The method further includes applying acoustic excitation to the pharmaceutical compound spray in order to produce spray particles of the desired size.

In yet another embodiment of the present subject matter, a method is provided for analyzing a characteristic of a pharmaceutical compound spray to be delivered to a patient from an inhaler device. The method includes measuring an overall acoustic emission pattern emitted by a pharmaceutical compound spray. The method further includes determining a selected characteristic of individual droplets comprising the spray based upon the overall acoustic emission pattern emitted by the spray.

In still another embodiment of the present subject matter, a method is provided for diagnosing spray particle size characteristics of a pharmaceutical compound spray. The method includes providing an inhaler device adapted to deliver a pharmaceutical compound spray to a patient. The method additionally includes measuring an overall acoustic emission pattern emitted by the pharmaceutical compound spray. The method further includes determining spray particle size distribution of individual droplets comprising the spray based upon the overall acoustic emission pattern emitted by the spray.

It is therefore an object of the present subject matter to provide methods of acoustic measurement and control of pharmaceutical sprays in order to enable greater control over the characteristics of pharmaceutical aerosols and facilitate improved quality and predictability of performance of pharmaceutical sprays.

An object of the present subject matter having been stated hereinabove, and which is addressed in whole or in part by the present subject matter, other objects will become evident as the description proceeds when taken in connection with the accompanying drawings as best described hereinbelow.

DETAILED DESCRIPTION

Figure 1:
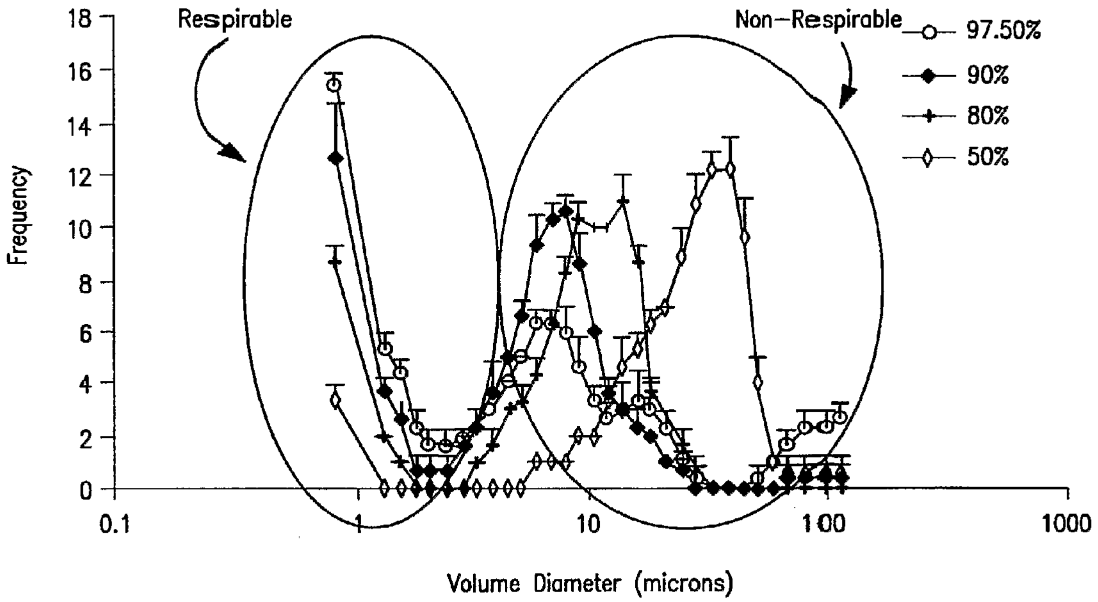
FIG. 1 is a chart showing particle size distributions of aerosol emitted from a prior art pressurized metered-dose inhaler (pMDI) containing propellant and ethanol.
Figure 2:
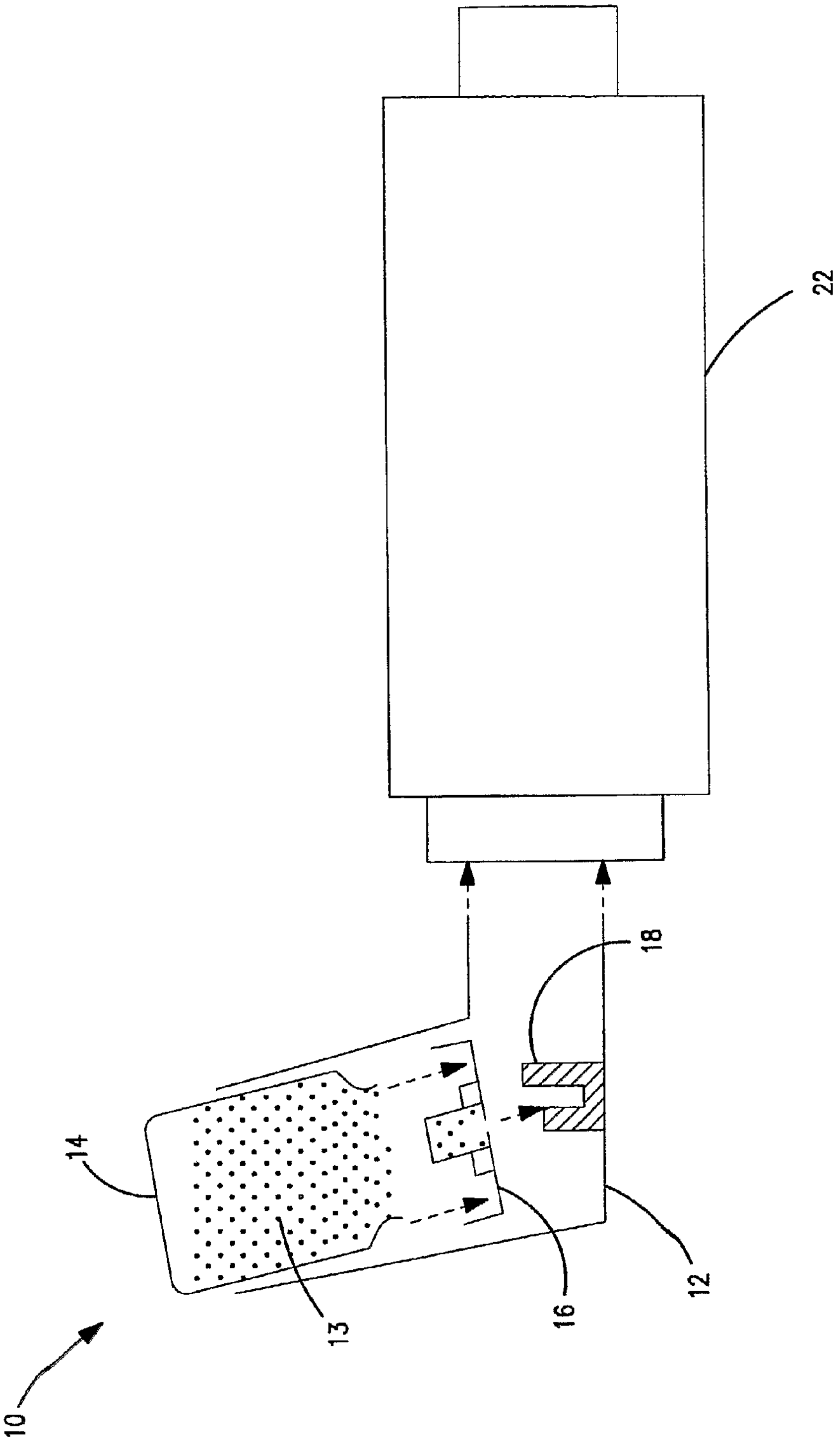
FIG. 2 is a schematic drawing of a prior art pressurized metered-dose inhaler (pMDI)
Figure 3:
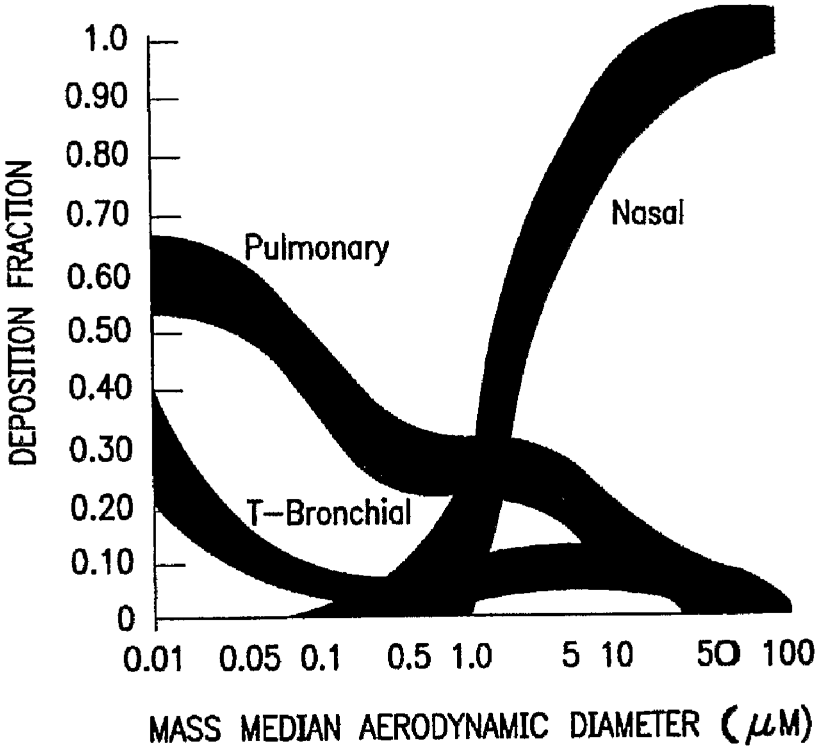
FIG. 3 is a chart showing regional lung deposition as a function of particle size.
Figure 4:
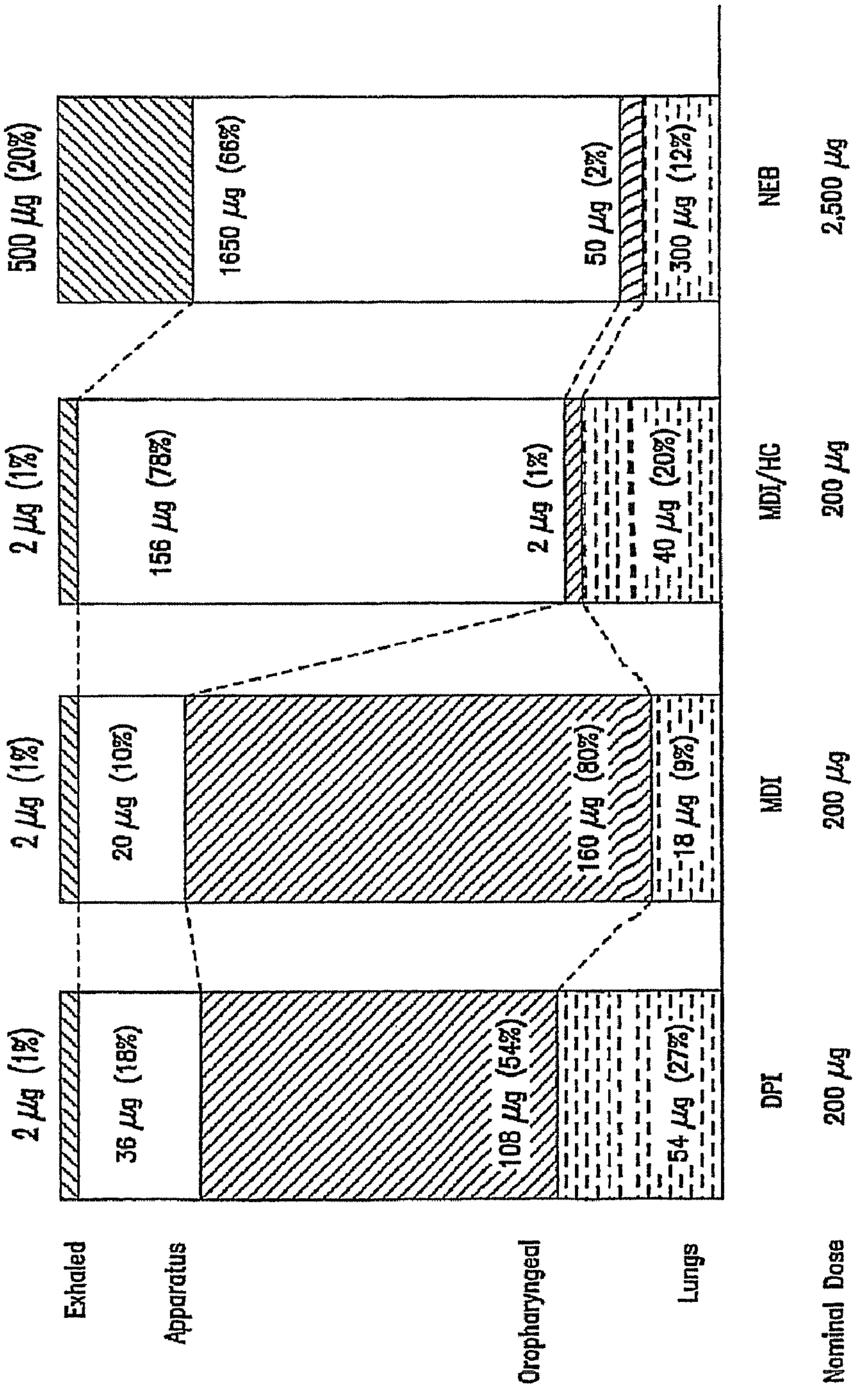
FIG. 4 is a chart showing a comparison of a nominal dose of albuterol deposited in the lungs, oropharynx, apparatus, and exhaled with typical use in a dry powder inhaler (DPI), a pressurized metered-dose inhaler (pMDI), a pMDI with holding chamber (MDI/HC), and a nebulizer (NEB)

While inhaled pharmaceutical aerosols are a common and rapidly growing drug delivery platform, it is well established that these inhaler systems are inefficient and a low proportion of the dose reaches the intended site of delivery (e.g., the lungs). This inefficiency is a direct result of broad particle size distributions where a significant fraction of droplets within the aerosol are too large to be respirable. The present subject matter is directed to the modulation of a characteristic (e.g., output efficiency, particle size distribution, etc.) of a pharmaceutical compound spray emitted from inhaler devices. In order to achieve improved prediction and control of a characteristic, such as spray particle size, the methods disclosed herein utilize acoustic techniques of measurement (direct diagnosis of energy dissipation during atomization) and also control (acoustic excitation of droplets). It is further envisioned in the present subject matter that synthesizing of the measurement and control aspects can be performed in order to form an active feedback system, foreseeably occurring within an inhaler device such as a pressurized metered-dose inhaler (pMDI), a dry powder inhaler (DPI), a nebulizer, or the like.

I. Aeroacoustics Analysis

The methods of the present subject matter are predicated upon aeroacoustics analysis. Aeroacoustics is the science of production of sound by fluid vibrations. The basic tenet of aeroacoustics is that sound waves have very small energy compared to typical fluid flows. For example, the threshold of hearing is at a sound intensity of $I_0=10^{-12}$ W/m$^2$ and the typical acoustic intensity of an inhaler spray is $I=10^{-7}$ W/m$^2$, whereas just the kinetic energy transport of the inhaler spray is $I=\rho u^3/2\cong 10^{-1}$ W/m$^2$. The perturbations of the flow field due sound waves can therefore be treated as small perturbations of the background flow velocity and pressure fields.

Although sound waves have small intrinsic energy, they can lead to significant modifications of droplet behavior due to resonance phenomena. An initial balance of energy analysis is useful in establishing that acoustic excitation is a feasible mechanism to induce droplet breakdown. A typical large drop let in an inhaler produced spray has a diameter of $D_0=10$ μm. The kinetic vibration energy of such a droplet undergoing oscillations with an amplitude equal to its diameter is approximately given by $E=\pi\rho D_0^5 f^2/12$ with f being the vibration frequency. At this amplitude, the oscillations are sufficiently energetic that breakup into smaller pieces becomes possible. Typical frequencies are in the range $10^2$ Hz<f<$10^3$ Hz so $E\cong 6\times 10^{-20}$ J. A typical pMDI dose leads to the production of $N\cong 2\times 10^{10}$ droplets. Assuming that resonance effects will lead to droplet breakup when 10 or more oscillations have been completed, one arrives at a required incident sound intensity of $I=NEf/(10\ \text{Å})\cong 10^{-8}$ W/m$^2$. This corresponds to excitation by sound waves with a noise intensity of NI=101 $g(I/I_0)\cong 80$ dB. Such acoustic excitation fields are relatively straightforward to produce, such as by shaping the inhaler nozzle to form a whistle of the appropriate frequency. As such, order-of-magnitude arguments based upon energy balances allow for acoustic control of inhaler droplet sizes.

The viability of the approach being established, one can turn to the issue of finding the functional form linking acoustic radiation to spray characteristics such as exit velocity, chamber pressure, and spray geometry. The equation governing the density perturbations ρ produced by acoustic sources is:

$$\frac{\partial^2 \rho}{\partial t^2} - a_0^2 \nabla^2 \rho = q$$

with q denoting the intensity of the sound sources. The above equation has a formal solution expressed as a convolution product:

$$\rho = q * G$$

$$\rho(\vec{x}, t) = \int q(\vec{y}, \tau) G(\vec{x} - \vec{y}, t - \tau) d\vec{y} d\tau$$

The nature of the acoustic sources can be used to estimate the above integral. Spray production entails drop formation and monopole acoustic sources. Drop oscillations are equivalent to dipole acoustic sources. The monopole sources are much more efficient acoustic radiators and dominate the overall acoustic field production. The resulting density perturbations produced by the acoustic field are:

$$\rho \sim \rho_0 m^2 \frac{l}{x}$$

assuming a compact source. Here $m=u/\alpha_0$ is the acoustic Mach number. The intensity of the resulting acoustic field is $I=\alpha_0^3\rho^2/\rho_0=\rho_0\alpha_0^3 m^4(l/x)$. Thus, a simple functional relation can be obtained predicting that the sound field emitted by the spray should vary as the fourth power of a parameter linked to the average droplet surface velocity during the process of droplet formation. Such functional forms can be constructed using more sophisticated arguments based upon experimental investigation of the spray formation process. Among the elements that can be included in the analysis are: balance between monopole terms and dipole terms; spatial interference patterns; and spatial directivity patterns.

It can be determined from the present subject matter that qualitative mathematical analysis guided by experimental input is capable of establishing links between the acoustic field emitted by a spray and the parameters characterizing the spray.

II. Study of Individual Droplet Vibrations

It is understood that analyzing of a selected characteristic, such as particle size, of a pharmaceutical compound spray in accordance with the subject matter disclosed herein can include measuring an overall acoustic emission pattern emitted by the spray. This measurement ca n include measuring acoustic emissions emitted by individual droplets comprising the spray. Additionally, controlling of the selected characteristic of the spray by acoustic excitation can include applying acoustic excitation to individual droplets comprising the spray. As such, a study of individual droplet vibrations was conducted.

When a droplet is set into vibration, the motion can be described as a superposition of spherical harmonics:

$$D(\theta, t) = D_0\left(1 + \sum_{l=1}^{r} c_l(t)P_l(\cos\theta)\right)$$

with $D(\theta, t)$ being the displacement along polar angle $\theta$ of the droplet surface (assuming axial symmetry). Droplet oscillations typically exhibit a reduced set of active vibration modes usually with $l<8$. An integral equation can be formulated for the velocity potential ø of an inviscid, incompressible droplet. The integral equation methods described were initially developed in work pertaining to bubbles. Though there are definite differences between bubbles and droplets, most notably relating to how the vibration problem is set up, the mathematical approach to formulating an integral equation description based upon potential flow and the numerical methods for solving such an integral equation are quite similar:

$$\phi(x) = \oint\left[G(x, y)\frac{\partial\phi}{\partial n}(y) - \phi(y)\frac{\partial G(x, y)}{\partial n}\right]dy$$

Capillary and unsteady effects enter through the unsteady Bernoulli equation:

$$\frac{D\phi}{Dt} = \frac{1}{2}(\nabla\phi)^2 - H + \gamma$$

$$H = \frac{d\alpha}{dt} + \frac{\sin\alpha}{r}$$

where H is twice the mean curvature of the axisymmetric bubble described by the parametric boundary curve (r(t), z(t)) in cylindrical coordinates; $\alpha$ is the angle of the tangent to the droplet to the radial axis and $\gamma$ is the overpressure due to incident acoustic fields. Units are chosen such that the surface tension equals unity. The droplet motion can be determined by solving the kinematic equation:

$$\frac{Dx}{Dt} = \nabla\phi$$

Figure 5:
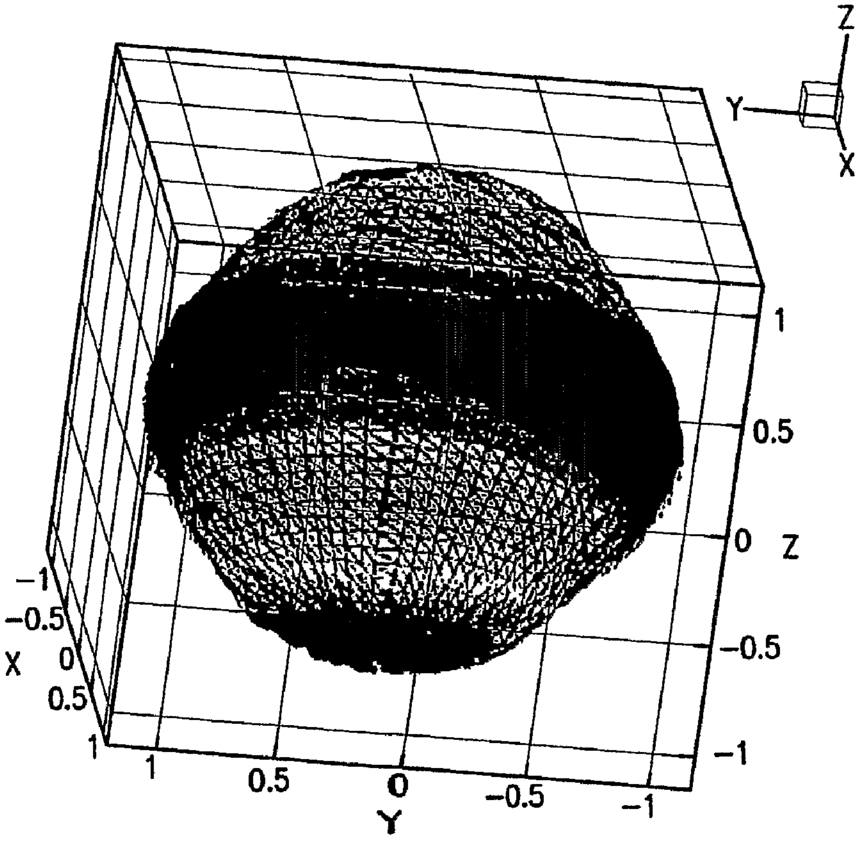
FIG. 5 is a charted perspective illustration of typical pharmaceutical compound spray droplet oscillations.
Figure 6:
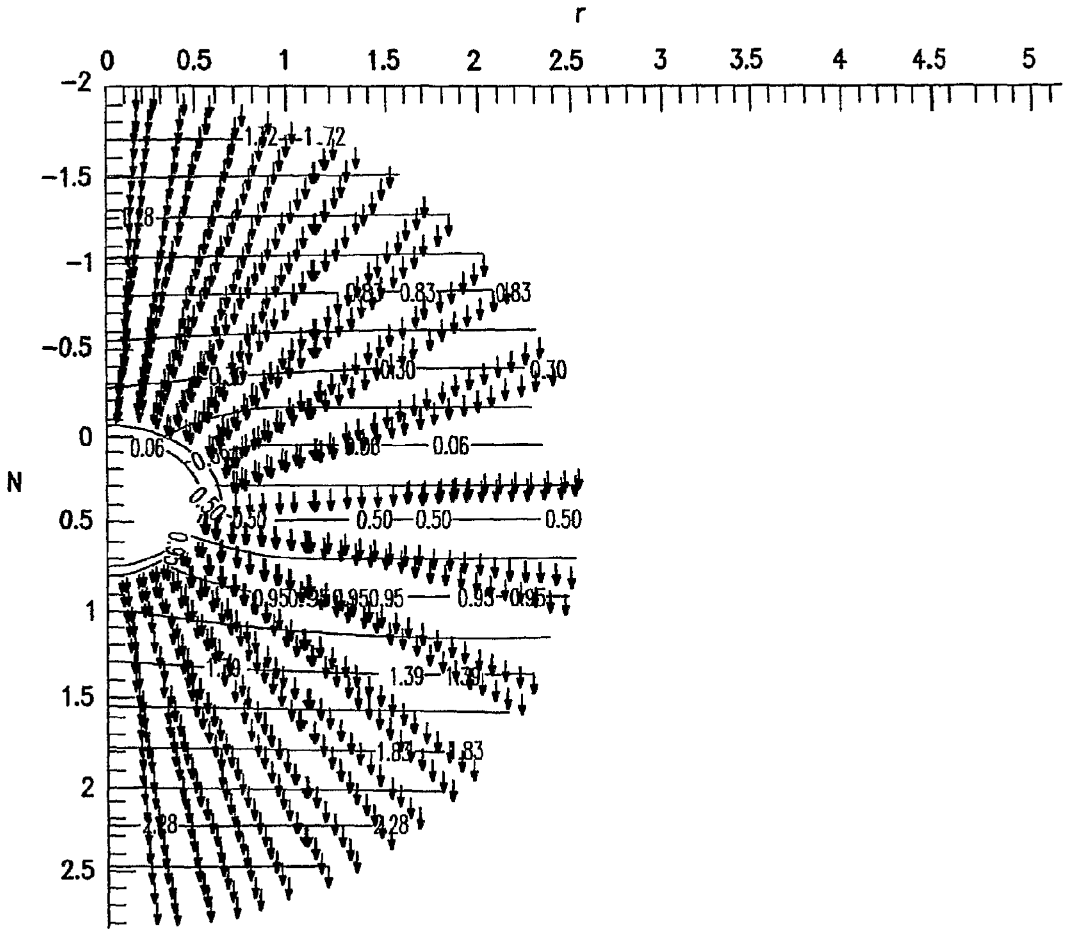
FIG. 6 is a chart showing the velocity field around a typical pharmaceutical compound spray droplet.

A typical snapshot of a droplet shape is depicted in FIG. 5 with the associated velocity field shown in FIG. 6. These computations were performed for an incident acoustic field of wavelength much larger than the droplet diameter. Such predictions are well verified experimentally for single-phase droplets or bubbles. The same procedures can be adapted to the more complicated case of the droplets in pharmaceutical sprays which may be multi-phase (e.g., with a solid inclusion) and with additional surface effects besides capillarity (e.g., surfactants). Droplet frequencies can be determined by positing a solution of the form $x=X\exp(i\omega t)$ and solving the resulting eigenproblem $i\omega X=K(X_0)X$ with $K(X_0)$ being the matrix resulting from a discrete approximation of the integral over the droplet surface given by instantaneous shape $X_0$.

III. Computing Overpressure on Droplets Produced by Incident Acoustic Waves

In order to determine a single droplet's motion or normal vibration modes under excitation by an external acoustic field as described herein, the pressure exerted by an incident acoustic wave $\gamma$ must be known. One could formulate an integral equation for this overpressure in the hypothesis of sound frequencies much larger than the droplet vibration frequencies, such that the droplet behaves compactly with respect to the incident sound field. However, the present subject matter contemplates a direct simulation of the propagation of an incident sound wave around a droplet by solving the wave equation:

$$p_{tt}-\nabla\cdot(\alpha^2(x, t)\nabla p)=0$$

Figure 7:
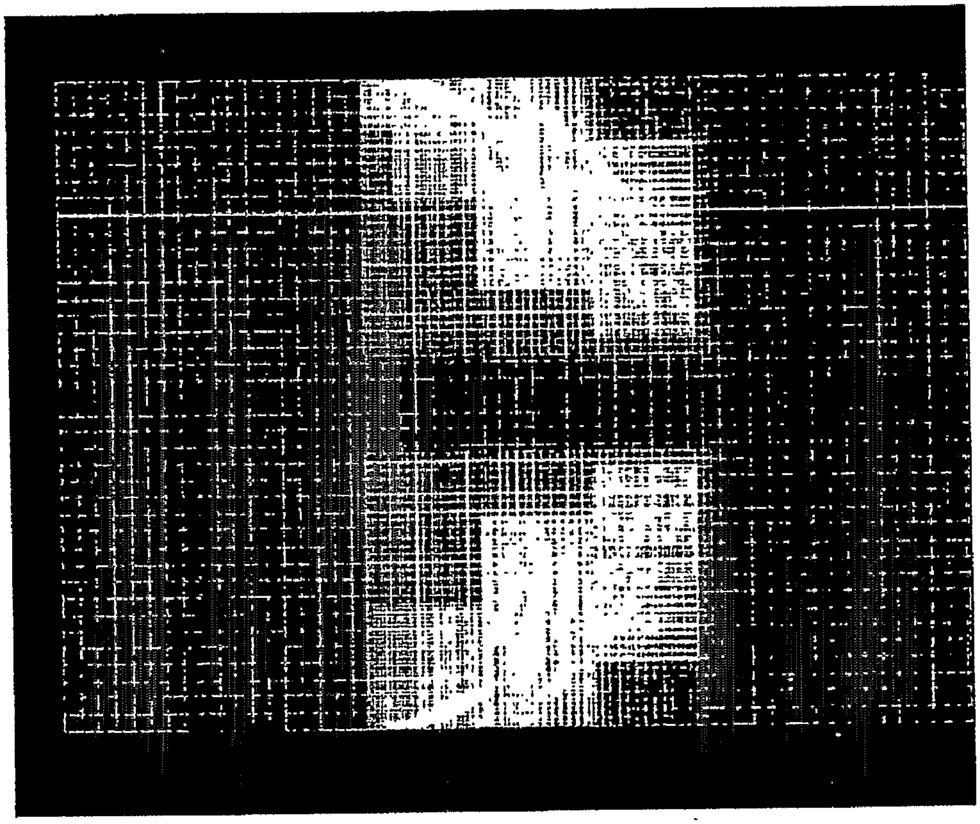
FIG. 7 is a plot showing an adaptive mesh computation of the acoustic field around a spherical inclusion modeling of a pharmaceutical compound spray droplet.

This is a conservation equation with spatially varying flux that is solved using a finite volume method. High-accuracy computations of solutions to this equation is contemplated (such as through the use of software) using an adaptive mesh refinement approach and local variations in acoustic impedance to model droplet positions. For example, FIG. 7 depicts a typical simulation result using adaptive mesh computation of the acoustic field around a spherical inclusion modeling a droplet. An incident planar wave impinges upon the droplet and is diffracted by the change in acoustic impedance. Additional grids are placed in regions of rapid variation of the acoustic field.

IV. Prediction of Maximum Sound Energy Absorption for Ellipsoidal Droplets

A prediction of maximum sound energy absorption for ellipsoidal droplets was made. Normal mode analysis of isolated ellipsoidal droplets leads to a prediction of the resonance frequency f which corresponds to the greatest accumulation of acoustic energy from an incident sound wave:

$$f = 0.86\frac{R_1}{R_2}\left(\frac{2\sigma}{\rho\pi^3 r^3}\frac{R_1}{r}\right)^{1/2}$$

where $R_1$, $R_2$, r are radii of ellipsoid of rotation and equivalent sphere radius, σ is superficial tension, and ρ is droplet density. This formula was obtained by a least square analysis of the results over a number of simulations of individual ellipsoidal droplet oscillating in mode l=2. It was determined that excitation at this frequency is most likely to lead to droplet breakdown when the accumulated energy becomes greater than the work of superficial tension forces that maintain the droplet volume. The present subject matter contemplates experimental results as defined below on the efficacy of this formula in predicting droplet breakdown due to external acoustic excitation.

V. Experimental Measurements

Figure 8:
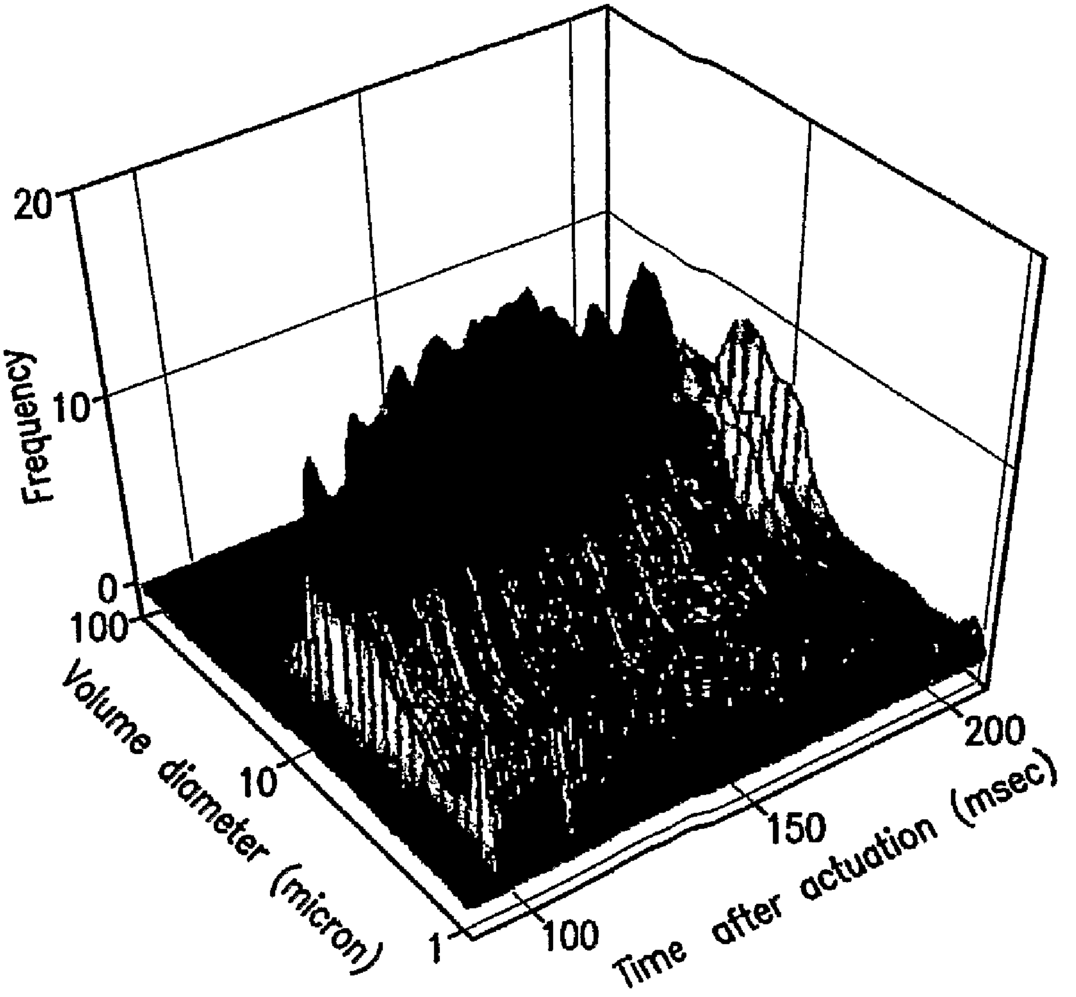
FIG. 8 is a particle size analysis chart showing the large droplet population distribution within pressurized metered-dose inhaler (pMDI) sprays measured in accordance with the present subject matter.

Regarding particle size analyses, particle size distributions of pMDIs containing typical formulations (HFA-134a and ethanol) were evaluated. FIG. 8 depicts a particle size analysis illustrating the presence of large droplet populations in pMDI sprays wherein two dominant particle size modes were identified at 1 and 10 μm or greater. Increasing propellant concentrations resulted in increases in the proportion of the size distributions at the 1 μm mode and also reduced the particle size of the larger droplet population. Droplets that constitute the larger mode in the particle size distribution (approximately 10 μm) are significant to inhaled therapy as they will undergo deposition in the mouth and throat via inertial impaction mechanisms instead of passing to the intended site of action in the lungs. In addition, large droplets carry significantly more drug mass than small droplets, making aerosol delivery inefficient.

Figure 9:
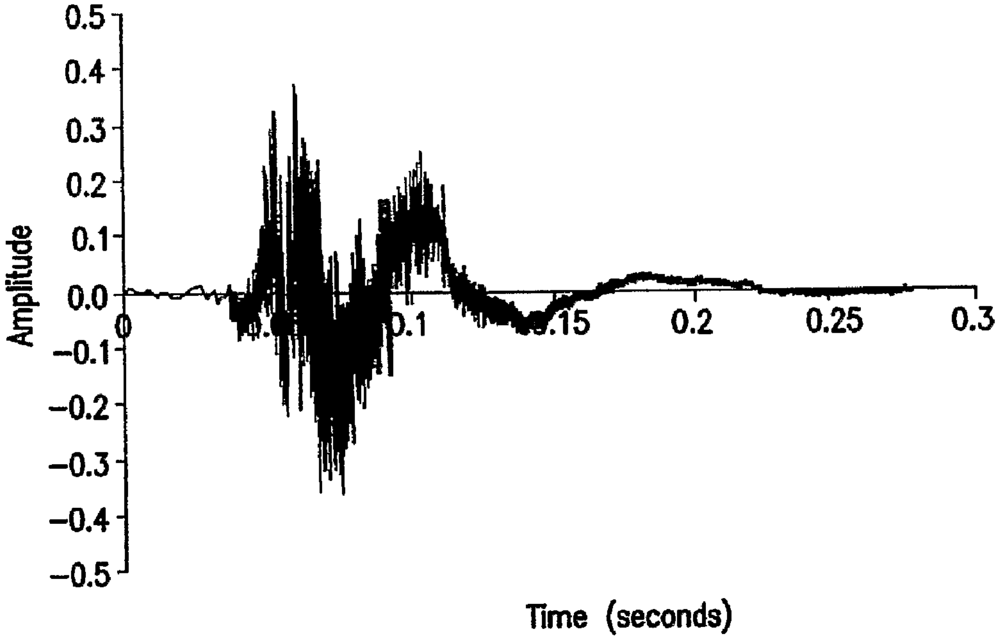
FIG. 9 is a chart showing a pressurized metered-dose inhaler (pMDI) acoustic emission measured in accordance with the present subject matter.

Preliminary measurements of acoustic emissions from pMDI sprays were additionally conducted. FIG. 9 is an illustration of a pMDI acoustic emission spectra as obtained in the experimentation. The acoustic emission signature is richly structured at several scales of inspection. When combined with the analysis presented above, the strong correlation between the observed acoustic signature and the particle size distribution within the spray is realized. Further time-series analysis was conducted and is described hereinafter.

VI. Results on Droplet Size Modulation Due to Acoustic Excitation

Additional experiments were conducted using modeling results from isolated droplet oscillations and acoustic excitation of individual droplets. A standard metered dose inhaler setup, similar to those commonly prescribed to patients, was used. The aerosol formulation was propellant only (no drug or excipients were used). While it is envisioned that a dose metering valve in the inhaler could be used, the aerosol in this experiment was generated using a continuous valve in the inhaler. This aspect facilitated longer particle size measurement times and ensured greater statistical validity of particle size measurements while avoiding the need to synchronize the transient spray with the particle sizing instrument.

Particle size measurements were performed using a laser diffraction instrument setup to analyze liquid droplet sprays from 5.8 μm to 180 μm. This particle size range was chosen due to the existence of a large particle mode (70 μm) that was suitable for modulation using the acoustic equipment as recited below.

In order to produce external acoustic excitation, a standard loudspeaker cone (30 watts max, 5.5 inches diameter) was connected to a home stereo amplifier (BSR McDonald) and an AGILENT 33120A 15 MHz function/Arbitrary Waveform Generator. The loudspeaker cone was focused to the intersection of the laser beam and the aerosol plume region. This region was acoustically insulated using a polystyrene housing covered with "egg-crate" packing foam.

Figure 10:
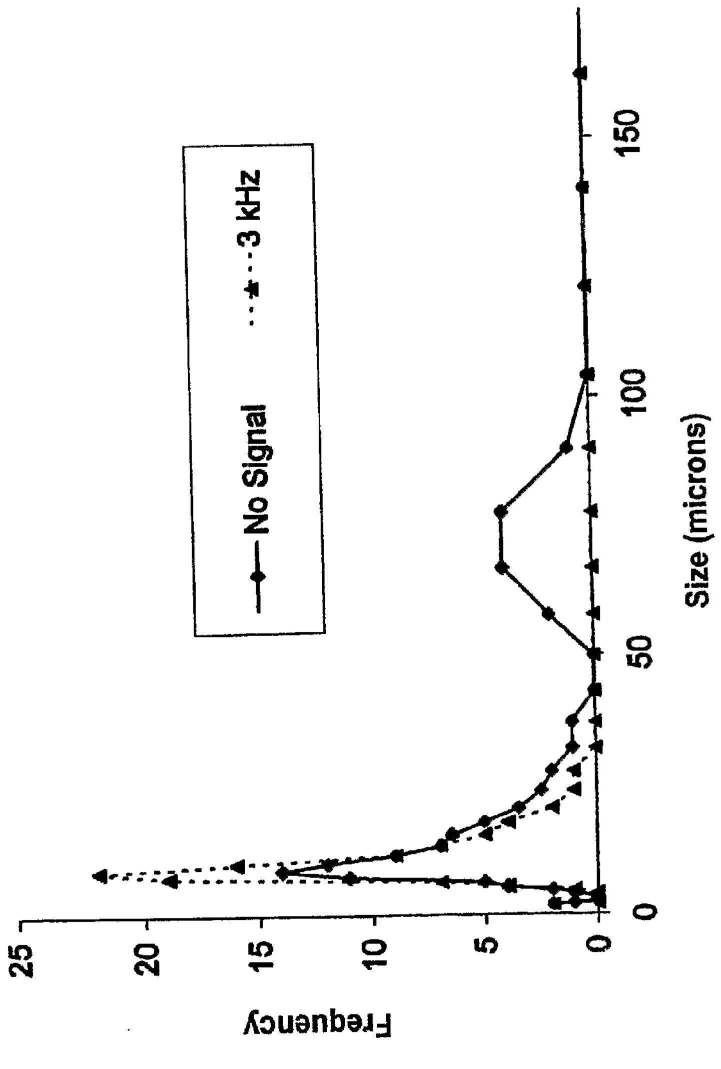
FIG. 10 is a chart showing the effect of acoustic excitation upon droplet size distribution in accordance with the present subject matter.
Figure 11:
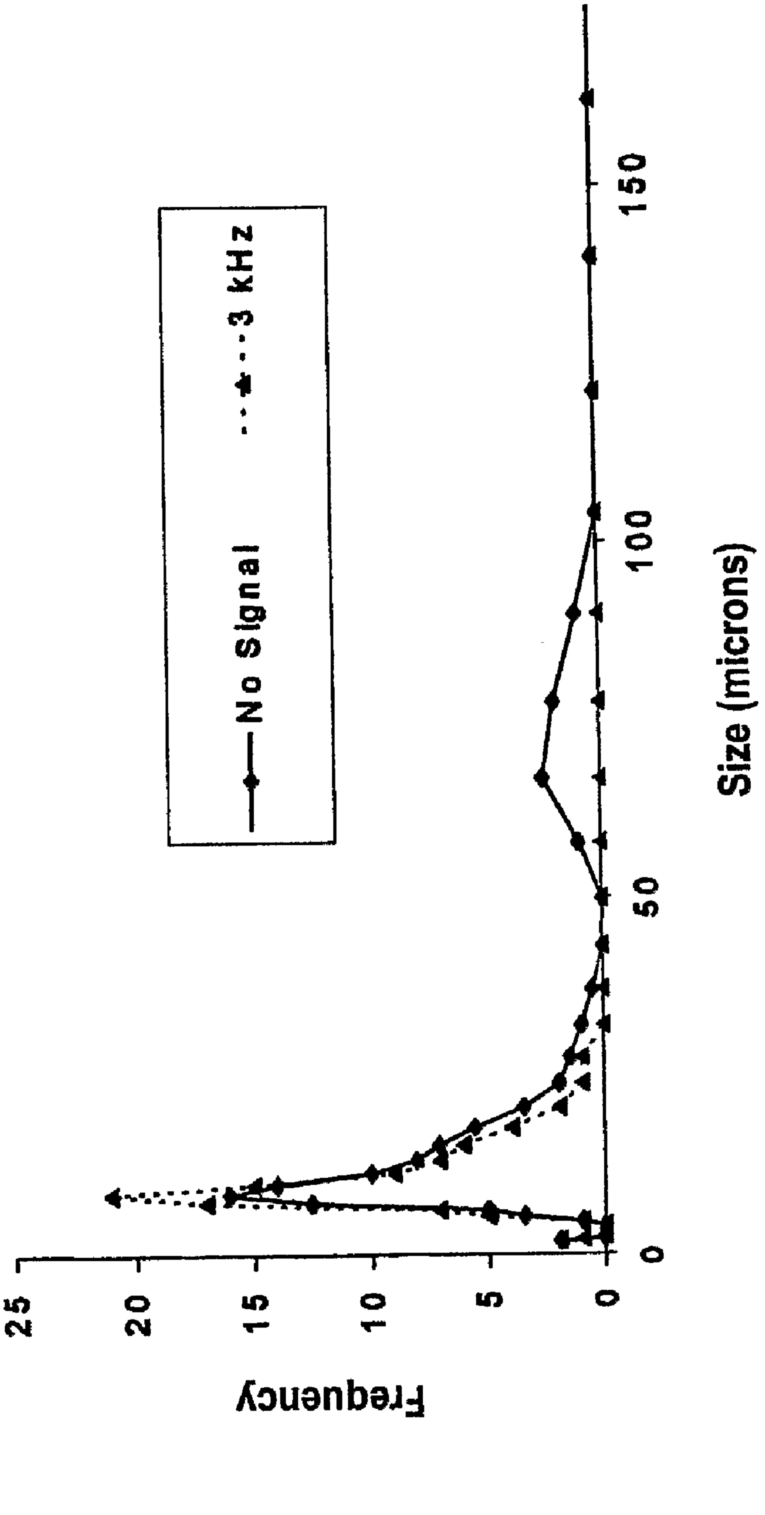
FIG. 11 is a chart showing the effect of acoustic excitation upon droplet size distribution at a different experimental realization than that charted in FIG. 10.
Figure 12:
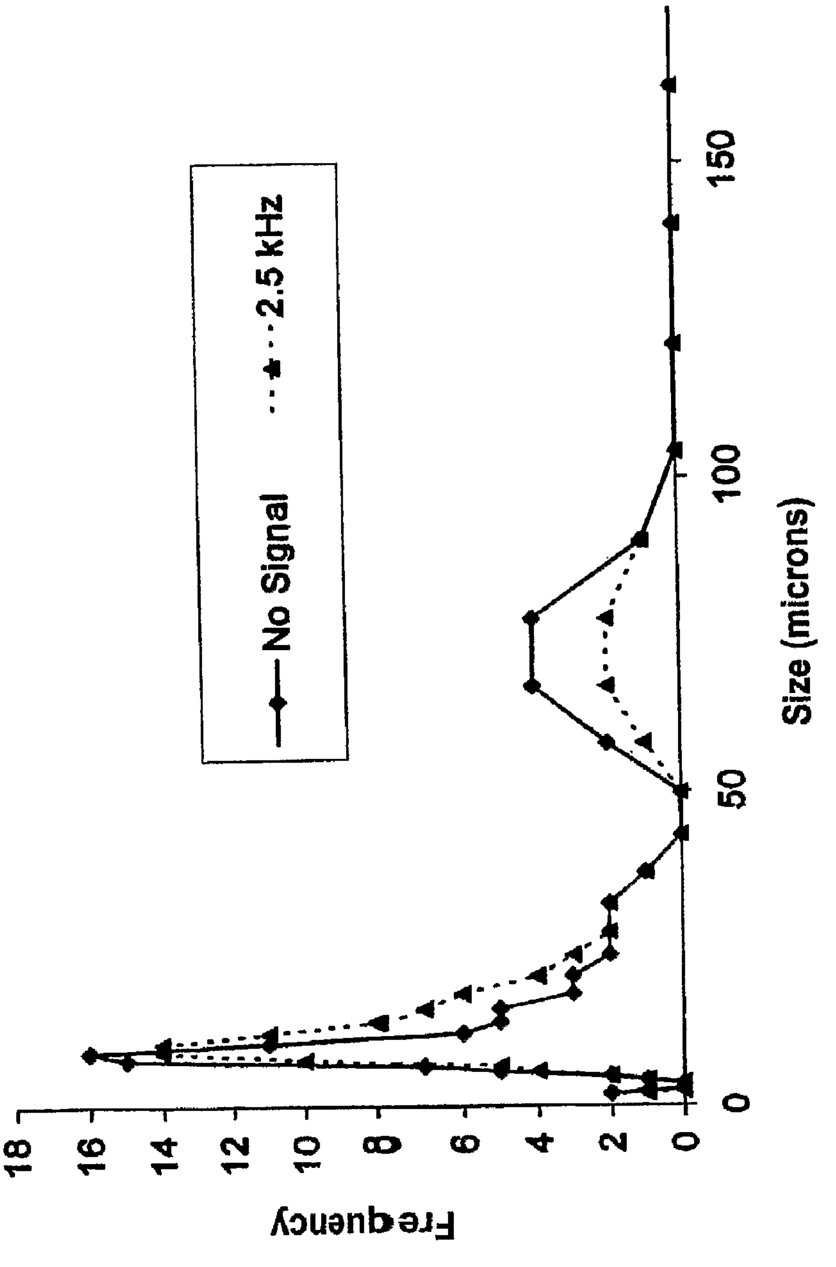
FIG. 12 is a chart showing the effect of acoustic excitation upon droplet size distribution at a different experimental realization and off-resonant excitation frequency than that charted in FIGS. 10-11.

Referring now to FIGS. 10-12, results of particle size distributions emitted from a metered dose inhaler under continuous valve emission as described above are shown.

The effect of acoustic excitation upon droplet size distribution is first shown in FIG. 10. The droplet sizes emitted by a metered dose inhaler were measured both before and after applying an acoustic signal with a frequency of 3 kHz as predicted by the formula for resonance frequency f as described above. The droplet distribution peak at ~75 microns is eliminated after application of acoustic excitation. A corresponding increase in smaller droplet sizes is observed.

Referring to FIG. 11, the effect of acoustic excitation upon droplet size distribution was produced similar to that in FIG. 10 but for a different experimental realization to highlight variability typically encountered in metered dose inhaler measurement. A droplet distribution peak is still observed at ~70 microns, but the distribution function shape differs from that shown in FIG. 11.

The effect of acoustic excitation upon droplet size distribution as shown in FIG. 12 is similar to that shown in FIGS. 10-11, but for a different experimental realization and off-resonant excitation frequency. The peak at 70 microns is diminished but not eliminated by excitation at off-resonance conditions.

As shown in FIGS. 10-12, acoustic excitation as contemplated by the present subject matter has an apparent influence on the particle size distribution of the spray. More particularly, the particle size mode located at approximately 70 μm is diminished upon application of a monochromatic acoustic signal of frequency predicted to correspond to resonance conditions of ellipsoids having an equivalent diameter of 70 μm and range of axis ratios $0.9 \leqq R_1/R_2 \leqq 1.1$. The peak is eliminated when this resonance frequency of approximately 3 kHz is applied. A test of off-resonance conditions was made by applying a slight frequency mismatch −2.5 kHz instead of 3 kHz. This diminishes but does not eliminate the 70 μm peak, highlighting the importance of resonance conditions and also confirming the validity of the normal mode analysis frequency prediction.

The experimental results discussed above highlight that normal mode analysis furnishes an accurate prediction of resonance, and acoustic excitation of moderate levels can modify droplet sizes within a pharmaceutical spray. In these experiments, the acoustic excitation of the aerosol spray was related to the frequency-response characteristics of the loudspeaker. It is understood that signal predictions must take into account the shape characteristics of droplets and differences between single-droplet and droplet cloud excitation. In addition, use of efficient loudspeakers, internal or external excitation, proper anechoic chamber conditions, and metered sprays rather than continuous systems can also affect resulting droplet size parameters.

The present subject matter contemplates the use of acoustic measurement and excitation to modify spray output parameters through acoustic modulation. Based on the physicochemical properties of the propellant to be optimized, device geometry, and measured aerosol output, predictions of droplet dynamics under acoustic excitation allow the selection of appropriate acoustic frequencies for spray modulation purposes. Based upon the subject matter disclosed herein, an acoustic signal (linear, non-linear, period, multi-period, etc.) derived from sound and acoustic emission analysis of sprays can be used to identify a complementary or disruptive signal that can be applied to the atomizer inhalation device such that control over atomization can be improved by these prediction and control steps.

It is believed that the discoveries of acoustic measurement and control of pharmaceutical sprays as described herein can be applied to the development of pharmaceutical devices for providing optimal lung deposition of aerosol particles. Most notably, in relation to spray particle size, the methods of the present subject matter can be used to produce a higher proportion of spray particles in an optimal distribution range of 1-5 microns in diameter than previous methods or devices.

It will be understood that various details of the present subject matter may be changed without departing from the scope of the present subject matter. Furthermore, the foregoing description is for the purpose of il lustration only, and not for the purpose of limitation.

What is claimed is:

1. A method of modulating a characteristic of a pharmaceutical compound spray, the method comprising the steps of:

a) analyzing a selected characteristic of a pharmaceutical compound spray utilizing acoustic measurement to develop corresponding acoustic data; and b) controlling the selected characteristic by applying acoustic excitation to the pharmaceutical compound spray in accordance with the acoustic data developed.

2. The method of claim 1 wherein analyzing of the selected characteristic comprises measuring an overall acoustic emission pattern emitted by the pharmaceutical compound spray.

3. The method of claim 2 wherein measuring of the overall acoustic emission pattern emitted by the pharmaceutical compound spray comprises measuring acoustic emissions emitted by individual droplets comprising the spray.

4. The method of claim 2 wherein measuring of the overall acoustic emission pattern emitted by the pharmaceutical compound spray is performed in an anechoic chamber.

5. The method of claim 2 wherein controlling the selected characteristic comprises applying acoustic excitation at a resonance frequency determined by the corresponding acoustic data from the overall acoustic emission pattern emitted by the pharmaceutical compound spray.

6. The method of claim 1 wherein controlling the selected characteristic comprises applying acoustic excitation to individual droplets comprising the pharmaceutical compound spray.

7. The method of claim 1 wherein the analyzed and controlled selected characteristic comprises an optimal spray particle size.

8. The method of claim 7 wherein the analyzed and controlled optimal spray particle size is in a distribution range of 1-5 microns in diameter.

9. A method of modulating spray particle size characteristics of a pharmaceutical compound spray, the method comprising the steps of:

a) analyzing spray particle size characteristics of a pharmaceutical compound spray by measuring an overall acoustic emission pattern emitted by the spray to develop corresponding acoustic data;

b) controlling the spray particle size characteristics by applying acoustic excitation to the pharmaceutical compound spray in accordance with the acoustic data developed; and c) synthesizing the analyzing and controlling steps, thereby forming an active feedback system.

10. The method of claim 9 wherein the analyzed and controlled spray particle size is in an optimal distribution range of 1-5 microns in diameter.

11. The method of claim 9 wherein measuring of the overall acoustic emission pattern emitted by the pharmaceutical compound spray comprises measuring acoustic emissions emitted by individual droplets comprising the spray.

12. The method of claim 9 wherein measuring of the overall acoustic emission pattern emitted by the pharmaceutical compound spray is performed in an anechoic chamber.

13. The method of claim 9 wherein controlling the spray particle size characteristics comprises applying acoustic excitation at a resonance frequency determined by the corresponding acoustic data from the overall acoustic emission pattern emitted by the pharmaceutical compound spray.

14. The method of claim 9 wherein controlling the spray particle size characteristics comprises applying acoustic excitation to individual droplets comprising the pharmaceutical compound spray.

15. A method of analyzing a characteristic of a pharmaceutical compound spray, the method comprising the steps of:

a) measuring an overall acoustic emission pattern emitted by a pharmaceutical compound spray; and b) determining a selected characteristic of individual droplets comprising the spray based upon the overall acoustic emission pattern emitted by the spray.

16. The method of claim 15 wherein measuring of the overall acoustic emission pattern emitted by the pharmaceutical compound spray comprises measuring acoustic emissions emitted by the individual droplets comprising the spray.

17. The method of claim 15 wherein measuring of the overall acoustic emission pattern emitted by the pharmaceutical compound spray is performed in an anechoic chamber.

18. The method of claim 15 wherein the selected characteristic comprises an optimal spray particle size.

19. The method of claim 18 wherein the optimal spray particle size is in a distribution range of 1-5 microns in diameter.

20. A method of analyzing spray particle size characteristics of a pharmaceutical compound spray, the method comprising the steps of:

a) providing a pharmaceutical compound spray;

b) measuring an overall acoustic emission pattern emitted by the pharmaceutical compound spray; and c) determining spray particle size distribution of individual droplets comprising the spray based upon the overall acoustic emission pattern emitted by the spray.

21. The method of claim 20 wherein measuring of the overall acoustic emission pattern emitted by the pharmaceutical compound spray comprises measuring acoustic emissions emitted by the individual droplets comprising the spray.

22. The method of claim 20 wherein measuring of the overall acoustic emission pattern emitted by the pharmaceutical compound spray is performed in an anechoic chamber.

23. The method of claim 20 wherein the spray particle size distribution is in an optimal range of 1-5 microns in diameter.

* * * * *